United States Patent [19]

Sprugel et al.

[11] Patent Number: 5,767,054
[45] Date of Patent: Jun. 16, 1998

[54] SURFACE DISINFECTANT AND CLEANING COMPOSITION

[76] Inventors: Friedrich A. Sprugel, Solalindenstrasse 36b, Munchen, Germany, D-81825; Eugen Eibofner, Vordere Au 13, Biberach, Germany, D-88400

[21] Appl. No.: 436,460

[22] PCT Filed: Sep. 29, 1994

[86] PCT No.: PCT/DE94/01159

§ 371 Date: Jul. 6, 1995

§ 102(e) Date: Jul. 6, 1995

[87] PCT Pub. No.: WO95/08917

PCT Pub. Date: Apr. 6, 1995

[30] Foreign Application Priority Data

Sep. 30, 1993 [DE] Germany ............ 43 33 385.0

[51] Int. Cl.[6] .................... C11D 3/48; C11D 7/30; A61K 31/11
[52] U.S. Cl. .................... 510/383; 510/108; 510/161; 510/191; 510/243; 510/394; 510/405
[58] Field of Search .................... 252/106, 107, 252/543, 170, 173, 174.11, 174.21, DIG. 1, DIG. 14; 510/383, 108, 161, 191, 243, 394, 405

[56] References Cited

U.S. PATENT DOCUMENTS

| | | | |
|---|---|---|---|
| 3,929,662 | 12/1975 | Boucher | 252/106 |
| 4,368,236 | 1/1983 | Frye | 428/412 |
| 4,540,505 | 9/1985 | Frazier | 252/106 |
| 4,689,168 | 8/1987 | Requejo | 252/139 |
| 4,764,302 | 8/1988 | Baker et al. | 252/301.23 |
| 5,256,328 | 10/1993 | Cavanagh et al. | 252/102 |
| 5,342,534 | 8/1994 | Skrobala et al. | 252/91 |
| 5,470,884 | 11/1995 | Corless et al. | 514/714 |

*Primary Examiner*—Paul Lieberman
*Assistant Examiner*—Lorna M. Douyon
*Attorney, Agent, or Firm*—Jacobson, Price, Holman & Stern, PLLC

[57] ABSTRACT

A surface disinfectant and cleaning composition includes (a) a biocidal agent selected from the group consisting of glyoxal, glutaraldehyde, and mixtures thereof, (b) 0.001 to 1% by weight of a fluoroaliphatic tenside selected from the group consisting of perfluoroalkanoic acids wherein the alkane residue has 1 to 10 carbon atoms, alkali and ammonium salts thereof, and mixtures thereof, (c) 0.002 to 5% by weight of at least one ultraviolet absorber, (d) 0.001 to 3% by weight of an optical brightener selected from the group consisting of benzotriazole derivatives, stilbene disulfonic acid derivatives, and mixtures thereof, and (e) a solvent selected from the group consisting of water, water-soluble alcohols, and mixtures thereof, and having a pH value of 2.5 to 5.0.

20 Claims, No Drawings

SURFACE DISINFECTANT AND CLEANING COMPOSITION

BACKGROUND OF THE INVENTION

The present invention relates to a surface disinfectant and cleaning composition, which contains a biocidal agent, a tenside and a solvent.

In a plurality of areas accessible to the public, such as means of transport, restaurants and, in particular, hospitals, homes, medical practises, and the like, it is necessary that those areas the people present there come into contact with should be freed from undesirable microorganisms. For this purpose, surface disinfectants are used which are frequently also combined with cleaning compositions and contain as a biocidal agent, for example, low-molecular alcohols, such as ethanol or propanol. These alcohols must be present in high concentration in order that they can develop their biocidal effect, as a result of which high concentration a fire hazard may occur and the surfaces treated with this disinfectant may be affected, for example, in that significant components are dissolved away, discoloration occurs, or the like.

From EP-A-0 384 126 there is known such a sprayable surface disinfectant based on lower aliphatic alcohols and anionic tensides, which contains a mixture of methyl alcohol and isopropanol, anionic tensides, an acidifier for adjustment of a pH value between 2 and 6, or an alkalizing agent for adjustment of a pH value between 8 and 12, the balance being water. This combination is said to be a composition, which rapidly achieves a bactericidal and fungicidal effect, exhibits good cleansing action and displays in spite of the purposefully low alcohol content good materials compatibility and a relatively high flash point and involves relatively quick drying and a low formation of residues.

DE-A-39 14827 describes a liquid disinfectant concentrate, which contains as a biocidal agent an active oxygen component, viz peroxymonosuiliric acid and/or the salts thereof, in addition to a tenside component and water as well as conventional additives.

It has been found that, when using the customary surface disinfectant and cleaning compositions, problems will occur specifically when synthetic material surfaces must be disinfected and cleaned. A particularly difficult situation arises in medical practises, and specifically, in dental practises where, due to legal provisions, a wide range of areas must be disinfected, specifically the treatment unit and the furniture and equipment. In surface disinfection of dental treatment units a problem arises from the fact that a wide variety of materials are used. The upholstery materials used must have a closed-cell surface so as to prevent germs from penetrating whereby they must usually consist of an integral foam, which is adhered onto a foam core. When treating such upholstery materials with an alcohol-containing disinfectant, often the plasticizers, colorants and stabilizers contained in the synthetic material are dissolved out, in consequence of which the surface coverings which often have been dyed pastel-colored turn unattractive, become discolored, or display cracks, very soon.

Difficulties arise also from the fact that in the case of the instrument trays which are often made of polycarbonate the disinfectants will cause cracks and discoloration, particularly in undercuts with metal threads inserted therein, which undercuts are difficult to reach. As a result of this, on account of the permanent treatment with the surface disinfectants changes of the surfaces of the materials treated will occur after a rather short time, which changes will be tolerated neither by personnel nor by patients.

SUMMARY OF THE INVENTION

The object of the present invention is to provide an efficient surface disinfectant and cleaning composition, which develops a strong disinfecting action against the germs usually encountered and provides a high tensidic cleaning effect while at the same time not causing any changes, discoloration or destruction of the surfaces of the synthetic materials treated therewith even when applied for a prolonged period of time.

It has been found that this object can be accomplished by the use of a surface disinfectant and cleaning composition, which contains a biocidal agent, a fluoroaliphatic tenside and a solvent.

Accordingly, the subject-matter of the present invention is the surface disinfectant and cleaning composition as claimed in the main claim. The subclaims relate to preferred embodiments of this subject-matter of the invention.

DETAILED DESCRIPTION OF THE INVENTION

The surface disinfectant according to the invention contains, as an essential component, a fluoroaliphatic tenside, in particular at least one perfluoroalkanoic acid in which the alkane residue has 1 to 10 carbon atoms and/or an alkali metal salt or an ammonium salt thereof This fluoroaliphatic tenside offers the special advantage that while being in very low concentration, it makes possible an almost perfect surface wetting, and excellently distributes the active ingredients of the disinfectant over the entire surface which is being treated, even in the case of surfaces that are difficult and are contaminated with blood and saliva as are encountered in the area of dental instruments and units.

As perfluoroalkanoic acids there are particularly preferred perfluoroalkyl carboxylic acids and/or perfluoroalkyl sulfonic acids, such as perfluorobutyric acid, trifluoromethane sulfonic acid and/or perfluorocaprylic acid, which acids are preferably applied in the form of alkali metal salts, such as potassium salts or ammonium salts.

The composition according to the invention preferably contains the said fluoroaliphatic tenside in a concentration of 0.001 to 1% by weight, and more preferably, in a concentration of 0.01 to 0.1% by weight, based on the composition actually applied, that is to say, the composition present in the final use concentration.

It has been found that the fluoroaliphatic tenside used in accordance with the invention is stable against ultraviolet radiation and does not attack the synthetic materials usually encountered, in particular synthetic covering materials, polycarbonate and acrylic resins, and also does not cause any stress corrosion cracking as often occurs when applying conventional surface disinfectants. Most of the products customary in the trade, which contain aryl sulfonates, fatty alcohol polyglycol ethers, quaternary ammonium salts as well as ethanolamines, when used for treatment of polycarbonate surfaces and acrylic resin surfaces for a rather long time, will result in cracks and discoloration. It has turned out now, surprisingly, that the fluoroaliphatic tenside applied in accordance with the invention will not cause such undesirable changes even if used in combination with an auxiliary tenside which shall be described more fully hereinafter.

As a biocidal agent the composition according to the invention preferably contains an aldehyde, a phenol derivative, a halogen phenyl derivative, a quaternary ammonium compound and/or an active oxygen-releasing compound, preferably, however, glyoxal and/or glutaraldehyde. It has been found that the last-mentioned aldehydes, unlike the usually applied quaternary ammonium derivatives, hemiformals, aryl phenols and phenyl phenols, arylamines and guanidines, in objects made of hard synthetic materials, such as polycarbonate, will not lead to any stress corrosion cracking and also will not cause any discoloration of the synthetic materials, though glyoxal exhibits in this respect an even better compatibility than does glutaraldehyde, for which reason glyoxal is most preferred as a biocidal agent.

As a solvent the composition according to the invention contains water and/or at least one water-soluble alcohol, such as ethanol, propanol and/or isopropanol, whereby more preferably a mixture of distilled water and ethanol, propanol or isopropanol or mixtures of these alcohols is applied, in particular at a ratio of water and alcohol, and the alcohol mixture respectively, of 20:80 to 80:20.

Preferably, the surface disinfectant and cleaning composition in accordance with the invention contains, in addition, at least one optical brightener, such as a benzotriazole derivative and/or a stilbene disulfonic acid derivative. Particularly preferred optical brighteners are 2-(2H-benzotriazole-2-yl)-4-methyl-6-dodecyl-phenol, a reaction product of 3-(3-(2H-benzotriazole-2-yl)-5-tert-butyl4-hydroxyphenyl)-propionic acid methyl ester and polyethylene glycol 300 and/or a bis(4,4'-triazinylamino)-stilbene-2,2'-disulfonic acid derivative (Uvitex BAM of the firm of Ciba-Geigy AG).

The composition according to the invention preferably contains these optical brighteners which, in particular, serve the purpose of not only keeping the appearance of the composition agreeable but also effecting a brighter look of the surfaces treated with the composition, in a concentration of 0.001 to 3% by weight, and more preferably, in a concentration of 0.01 to 0.5% by weight, this concentration again being the final use concentration.

Furthermore, it is advantageous to further add to the surface disinfectant and cleaning composition according to the invention at least one UV absorbent, for instance, a UVA/UVB absorbent, or only a UVA absorbent, so as to prevent in this way, specifically in the cleansing spraying and wiping disinfection of particularly sensitive imitation leathers, ageing and discoloration in that active substances contained in the surface treated, which substances have inevitably been dissolved away from the surface, are re-supplied to the surface. The fluoroaliphatic tenside used according to the invention causes the above-mentioned optical brighteners, and also the UV absorbents, to remain, in the form of a very thin film, on the surface of the synthetic materials treated, thus producing a kind of depot effect when applied constantly. In this manner it becomes possible to keep the sensitive synthetic material surfaces practically in their original state for considerably longer periods of time, which was not achievable with the surface disinfectants heretofore applied.

As a UV absorbent there are preferably used in accordance with the invention p-aninobenzoic acid derivatives, benzmidazole derivatives, benzophenone derivatives, benzoxazole derivatives, camphor derivatives, coumarin derivatives, dibenzoyl methane derivatives, gallic acid derivatives, o-hydroxybenzoic acid derivatives, cinnamic acid derivatives and/or p-methoxycinnamic acid derivatives, wherein there are most preferably applied 2-hydroxy-4-methoxy-benzophenone, 2,4-dihydroxybenzophenone and/or 2-hydroxy4-methoxy-benzophenone-5-sulfonic acid.

The composition according to the invention contains the said UV absorbent preferably in a concentration of 0.002 to 5% by weight, and more preferably, in a concentration of 0.02 to 1% by weight, again referred to the composition actually applied.

According to the invention, in order to further improve the cleaning composition, it is possible, without impairing the disinfecting and preservative effect, to further add at least one nonionic or anionic auxiliary tenside, for instance a nonionic auxiliary tenside in the form of an alkynol, an alkyne diol and/or an ethylene oxide derivative thereof, such as, for instance, 3,5-dimethyl-1-hexine-3-ol and 2,4,7,9-tetramethyl-5-decine-4,7-diol. As an anionic tenside there may be preferably used allyl sulfates or alkyl sulfonates having 8 to 18 carbon atoms in the alkyl residue, which are preferably employed in the form of the sodium or ammonium salts. This auxiliary tenside can be present in an amount, which is as much as 5-fold the amount of the fluoroaliphatic tenside, without impairing the desired disinfecting, cleaning and preservative effect. Preferably, this auxiliary tenside is contained in an amount of 0.001 to 5% by weight, more preferably 0.1 to 2.0% by weight.

It is, of course, possible, furthermore, to incorporate in the surface disinfectant and cleaning composition according to the invention conventional additives, such as corrosion inhibitors, stabilizers, colorants, perfume components and/or aromas.

The composition according to the invention, in the form in which it is being used, preferably has a pH value of 2.5 to 5.0, since the best disinfecting effect is achievable within the acidic range. Advantageously, the composition according to the invention is adjusted to a pH value of 3.0 to 4.5 by the use of ammonia, sodium hydroxide, potassium hydroxide, a morpholine derivative and/or a short-chain amine or the fluoroalkanoic acid which is used as a fluoroaliphatic tenside.

The composition according to the invention may be provided in the form in which it is ultimately applied by the user to disinfect and clean the surfaces, which are to be treated, but it may also be provided in the form of a concentrate, which, prior to use, is diluted to the application concentration with the aforementioned solvent, that is, for instance, distilled water and/or the low-molecular alcohols. Accordingly, the subject-matter of the invention also is a surface disinfectant and cleaning composition, which contains the above-mentioned components and is present in the form of a concentrate having such increased concentration as to yield, on dilution with the solvent, the final use concentrations as quoted.

The surface disinfectant and cleaning composition according to the invention is useful for disinfection in a wide variety of fields, for example, surfaces, apparatuses, instruments and furniture in medical areas, especially in dental practises, in industrial and commercial areas, as well as in household, kitchen, sanitary and veterinary areas. For example, the surface disinfectant according to the invention is useful for the personal disinfection of toilets, wash basins, seats, or the like which are used by a large number of people, such as, for instance, public toilets, especially in trains, ships and airplanes.

The surface disinfectant according to the invention is disinfecting and antistatic, kills bacteria, inclusive of tubercle bacilli hepatitis B viruses, HIV viruses, and fungi on wood, synthetic material and other surfaces, makes possible the cleaning of coverings made of synthetic material, furniture covered with synthetic material, while at the same time being gentle to the material both in metals and in synthetic materials, such as polyvinyl chloride, polycarbonate, acrylic resins and alcohol-sensitive lacquers, and offers, in addition, the advantage that the components, which are preferably contained therein, are harmless and readily biodegradable.

The following examples serve to further illustrate the invention.

EXAMPLE 1

Surface Disinfectant Concentrate

The components of this concentrate are given in the table below:

| Component | wt. % |
|---|---|
| 40% Glyoxal in water | 68 |
| Sodium alkyl sulfate (Sulfetal FH 40) | 22 |
| 50% Potassium perfluoro octoate | 6 |
| Bouquet Rose (perfume) | 2 |
| 2-Hydroxy-4-methoxy-benzophenone | 1.2 |
| Optical brightener (Uvitex BAM) | 0.8 |
|  | 100 |

In examining this concentrate in accordance with the guidelines of the German Society for Hygiene and Microbiology Deutsche Gesellschaft für Hygiene und Mikrobiologie), it was found that, on dilution with distilled water to a concentration of 7.5% and higher, this concentrate yields a complete bacteriostatic and fungistatic effectiveness against *Staphylococcus aureus, Streptococcus faecalis, Escherichia coli, Proteus mirabilis, Pseudomonas aemginosa*, and *Candida albicans*. On applying this concentrate, which has been diluted with distilled water to a concentration of 25%, a bactericidal and fungicidal effect is achieved after a contact time as short as five minutes.

It has been found, furthermore, that this composition is also effective against HIV and HBV viruses.

EXAMPLE 2

By diluting the concentrate specified in example 1, the surface disinfectant and cleaning composition in the use form as described below is obtained:

| Component | wt. % |
|---|---|
| Concentrate of example 1 | 4.80 |
| Ethanol (96%) | 25.00 |
| 1-Proanol, pure | 35.00 |
| Distilled water free of salt | 35.20 |
|  | 100.00 |

By adjusting the pH value to a pH value of 4 by the use of perfluorocaprylic acid the ready-to-use finished product is obtained. For use, this finished product is preferably sprayed, by means of a spraying device, onto the surfaces to be treated and is wiped off with a cloth whereby there results an excellent cleansing effect and, at the same time, disinfection and preservation of the synthetic material surfaces treated is achieved. It has been found that this surface disinfectant and cleaning composition also prevents ageing and discoloration in the case of imitation leathers, which are particularly sensitive and, for example, have been dyed pastel-colored, this prevention being accomplished in that the active ingredients and stabilizers which have been dissolved away from the surface as a result of the constant cleaning with alcohol and tensides are resupplied in the form of UV absorbents and surface active agents contained in the composition according to the invention by being applied in the shape of a micro-thin film which, in each cleansing operation, is not removed but constantly replenished.

By combining the fluoroaliphatic tenside with the UV absorbents preferably used in accordance with the invention and the preferably employed biocidal agent glyoxal there is provided a highly active composition which is producible at low cost and which makes possible a hitherto unknown protection of the sensitive synthetic material surfaces, which are to be treated therewith, in particular, synthetic material coverings of furniture in medical practises. Since the raw materials contained in this preferred composition have been fully tested in the cosmetic field, also no harmful effects on the handling personnel are to be expected.

The active ingredients contained in this preferred composition according to the invention are readily biodegradable, easy to dispose of and, thus, beneficial to the environment. Moreover, the active ingredients contained in the composition are colorless, and odorless in the final use concentrations; thus, there results a surface disinfectant and cleaning composition which has an unexpectedly advantageous combination of desirable application properties.

We claim:

1. A surface disinfectant and cleaning composition consisting essentially of (a) an effective biocidal amount of a biocidal agent selected from the group consisting of glyoxal, glutaraldehyde, and mixtures thereof, (b) 0.001 to 1% by weight of a fluoroaliphatic tenside selected from the group consisting of perfluoroalkanoic acids wherein the alkane residue has 1 to 10 carbon atoms, alkali and ammonium salts thereof, and mixtures thereof, (c) 0.002 to 5% by weight of at least one ultraviolet absorber, (d) 0.001 to 3% by weight of an optical brightener selected from the group consisting of benzotriazole derivatives, stilbene disulfonic acid derivatives, and mixtures thereof, the balance (e) being a solvent selected from the group consisting of water, water-soluble alcohols, and mixtures thereof, and optionally: (f) at least one nonionic or anionic auxiliary tenside, and (g) at least one perfume component, said composition having a pH value of 2.5 to 5.0.

2. The composition according to claim 1, wherein the perfluoroalkanoic acid is a perfluoroalkyl carboxylic acid, a perfluoroalkyl sulfonic acid, or a mixture thereof.

3. The composition according to claim 1, wherein the perfluoroalkanoic acid is perfluorobutyric acid, trifluoromethane sulfonic acid, perfluorocaprylic acid, or a mixture, thereof.

4. The composition according to claim 1, wherein the fluoroaliphatic tenside concentration is 0.01 to 0.1% by weight.

5. The composition according to claim 1, wherein the water-soluble alcohol is ethanol, propanol, isopropanol, or a mixture thereof.

6. The composition according to claim 5, wherein the solvent is a mixture of (i) distilled water and (ii) at least one of ethanol, propanol, and isopropanol, at a ratio of 20:80 to 80:20.

7. The composition according to claim 1, wherein the optical brightener is 2-(2H-benzotriazole-2-yl)-4-methyl-6-dodecylphenol, a reaction product of 3-(3-(2H-benzotriazole-2-yl)-5-tert-butyl-4-hydroxyphenyl)-propionic acid methyl ester and polyethylene glycol 300, a bis(4,4'-triazinylamino)-stilbene-2,2'-disulfonic acid derivative, or a combination thereof.

8. The composition according to claim 1, wherein the optical brightener concentration is 0.01 to 0.5% by weight.

9. The composition according to claim 1, wherein the UV absorbent is a p-aminobenzoic acid derivative, a benzimidazole derivative, a benzophenone derivative, a benzoxazole derivative, a camphor derivative, a coumarin derivative, a dibenzoylmethane derivative, a gallic acid derivative, an o-hydroxybenzoic acid derivative, a cinnamic acid derivative, a p-methoxycinnamic acid derivative, or a combination, thereof.

10. The composition according to claim 9, wherein the UV absorbent is 2-hydroxy-4-methoxy-benzophenone, 2,4-dihydroxybenzophenone, 2-hydroxy-4-methoxy-benzophenone-5-sulfonic acid, or a combination thereof.

11. The composition according to claim 1, wherein the UV absorbent concentration is 0.02 to 1% by weight.

12. The composition according to claim 1, wherein said at least one nonionic or anionic auxiliary tenside is present.

13. The composition according to claim 12, wherein the auxiliary tenside is a nonionic alkynol, alkyne diol, ethylene oxide adduct thereof, or a combination thereof.

14. The composition according to claim 13, wherein the alkynol is 3,5-dimethyl-1-hexine-3-ol, and the alkyne diol is 2,4,7,9-tetramethyl-5-decine-4,7-diol.

15. The composition according to claim 12, wherein the auxiliary tenside is an anionic alkyl sulfate or alkyl sulfonate, in which the alkyl residue has 8 to 18 carbon atoms.

16. The composition according to claim 8, wherein the auxiliary tenside concentration is 0.1 to 2.0% by weight.

17. The composition according to claim 1, wherein said at least one perfume component.

18. The composition according to claim 1, having a pH value of 3.0 to 4.5.

19. The composition of claim 18, wherein the pH of 3.0–4.5 is effected by the perfluoroalkanoic acid.

20. The composition of claim 18, wherein the pH of 3.0–4.5 is effected by ammonia, sodium hydroxide, potassium hydroxide, a morpholine derivative, a short-chain amine, or a combination thereof.

* * * * *

UNITED STATES PATENT AND TRADEMARK OFFICE
CERTIFICATE OF CORRECTION

PATENT NO. : 5,767,054
DATED : June 16, 1998
INVENTOR(S) : Friedrich A. SPRÜGEL and Eugen EIBOFNER It is certified that error appears in the above-indentified patent and that said Letters Patent is hereby corrected as shown below:

On the cover page of the patent, line 1 of item "[76]," change the spelling of the first-named inventor's last name to --Sprügel--.

Signed and Sealed this

Fifteenth Day of December, 1998

Attest:

BRUCE LEHMAN

*Attesting Officer*          *Commissioner of Patents and Trademarks*